United States Patent [19]

Pace et al.

[11] Patent Number: 5,762,635
[45] Date of Patent: Jun. 9, 1998

[54] RETRACTABLE NEEDLE SYRINGE

[76] Inventors: Paul A. Pace, 610 67th St., 2nd Floor Front, Brooklyn, N.Y. 11220; John J. Riddle, 7804 3rd Ave., Brooklyn, N.Y. 11209

[21] Appl. No.: 800,956

[22] Filed: Feb. 18, 1997

[51] Int. Cl.⁶ ............................................. A61M 5/00
[52] U.S. Cl. ................................... 604/195; 604/218
[58] Field of Search .......................... 604/195, 192, 604/187, 198, 110, 218

[56] References Cited

U.S. PATENT DOCUMENTS

| | | | |
|---|---|---|---|
| 4,919,657 | 4/1990 | Haber et al. | 604/232 |
| 4,950,251 | 8/1990 | Haining | 604/195 |
| 5,061,249 | 10/1991 | Campbell | 604/195 |
| 5,098,402 | 3/1992 | Davis | 604/195 |
| 5,188,601 | 2/1993 | King | 604/110 |
| 5,190,526 | 3/1993 | Murray et al. | 604/110 |
| 5,484,414 | 1/1996 | Pace | 604/110 |

*Primary Examiner*—John D. Yasko
*Attorney, Agent, or Firm*—Richard L. Miller, P.E.

[57] ABSTRACT

A retractable needle syringe that includes a barrel assembly, a plunger assembly, and a needle assembly. The plunger assembly is movably mounted in the barrel assembly. And, the needle assembly is movably mounted in the barrel assembly and engagable with the plunger assembly, so that after the retractable needle syringe has been used, the plunger assembly is engaged with the needle assembly, the plunger assembly is pulled, and the needle assembly is drawn into the barrel assembly.

20 Claims, 2 Drawing Sheets

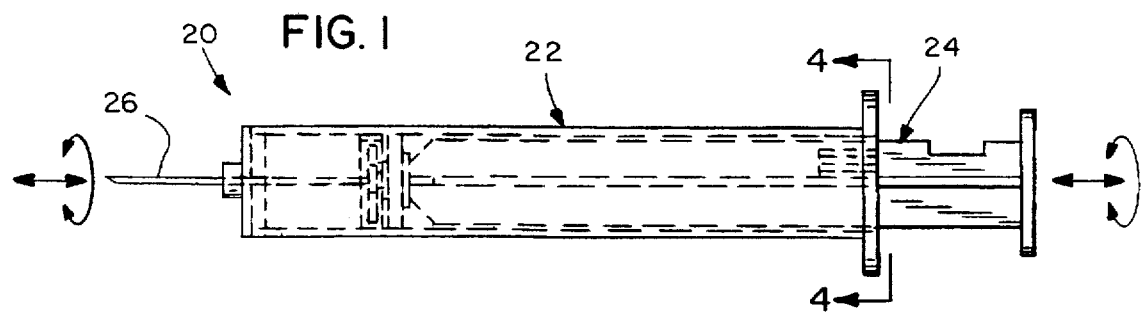
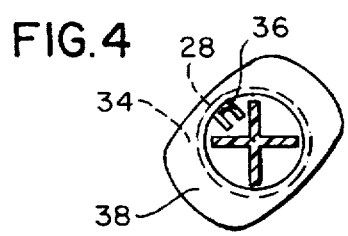
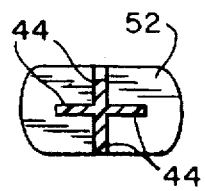
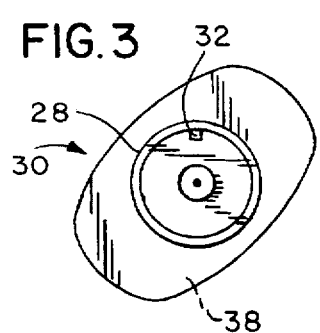
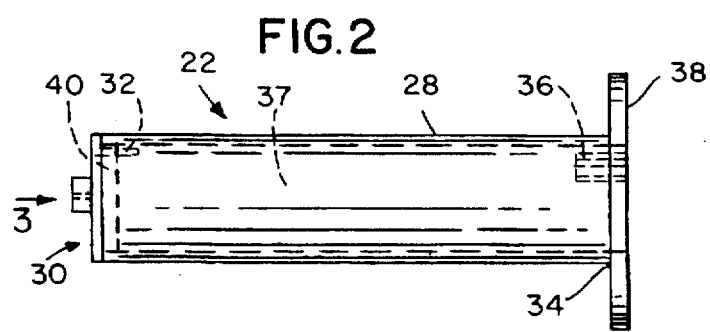

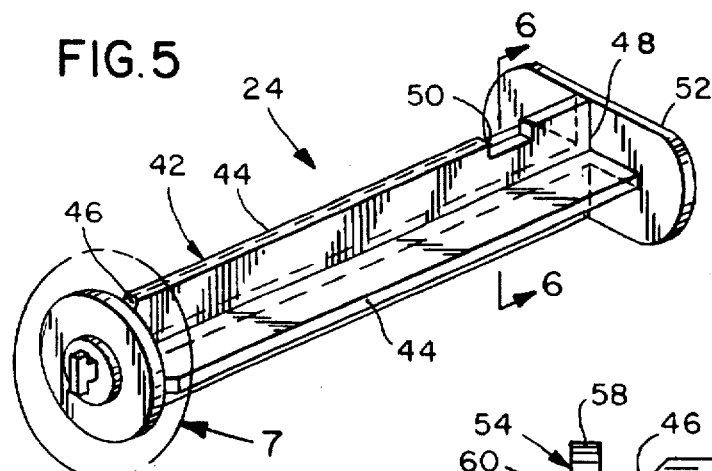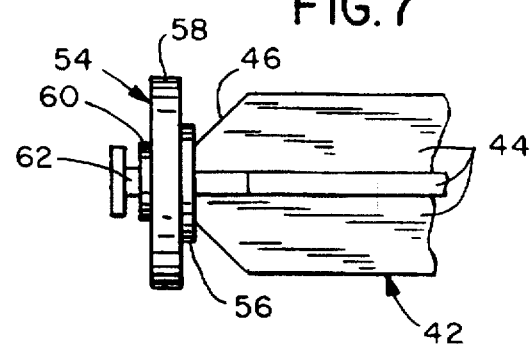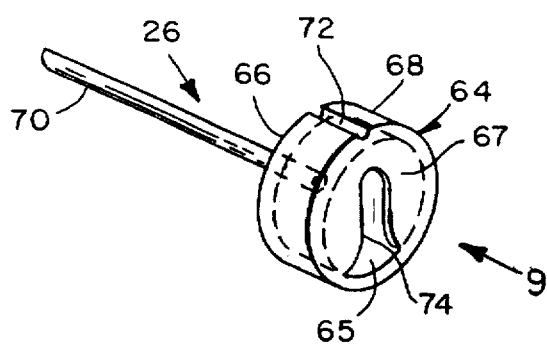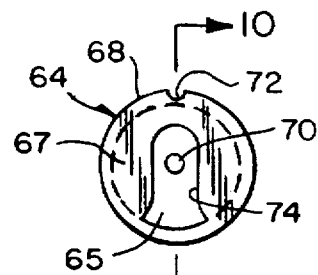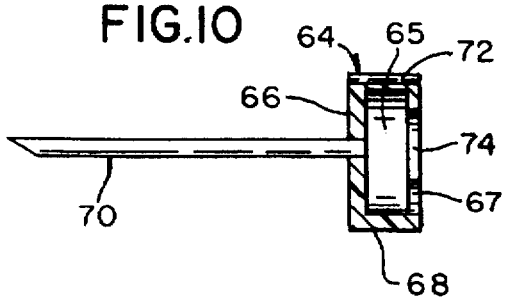

RETRACTABLE NEEDLE SYRINGE

BACKGROUND OF THE INVENTION

1. Field of the Invention

The present invention relates to a syringe. More particularly, the present invention relates to a syringe with a retractable needle.

2. Description of the Prior Art

As a result of the recent and rapid spread of communicable diseases, such as AIDS and Hepatitis, the need for a safe, self-contained syringe with a retracting needle is apparent. Health care workers such as doctors, nurses, lab analysts and the like are constantly faced with the threat of contracting such diseases via contaminated blood which may be present on the end of a needle which might accidentally puncture their skin. Sanitation and medical waste disposal personnel are also faced with the same danger.

In addition, the costs of disposing of conventional syringes is becoming prohibitive, since they must be transported in thick plastic receptacles, handled with extreme care, and disposed of in only designated waste facilities.

Furthermore, conventional syringes are a large contributor to the spread of diseases such as AIDS and Hepatitis among intravenous drug users. By re-using syringes with contaminated needles, these drug users have greatly increased the spread of blood transported infectious diseases.

The incidence of injury to life and health by the spread of infected blood present on syringe needles is greater today than ever before. The need for a safe, reliable, inexpensive and manufacturable syringe with a retractable needle is of significant importance.

Numerous innovations for retractable needles have been provided in the prior art that will be described. Even though these innovations may be suitable for the specific individual purposes to which they address, however, they differ from the present invention.

FOR EXAMPLE, U.S. Pat. No. 4,919,657 to Haber et al. teaches a reusable dental syringe having a retractable needle.

ANOTHER EXAMPLE, U.S. Pat. No. 4,950,251 to Haining teaches a retractable needle syringe.

STILL ANOTHER EXAMPLE, U.S. Pat. No. 5,190,526 to Murray et al. teaches a hypodermic syringe having a complicated needle retracting system requiring many working parts.

FINALLY, YET ANOTHER EXAMPLE, U.S. Pat. No. 5,484,414 to Pace teaches a syringe with a retractable needle, comprising a syringe body having a bore, a needle assembly within the bore, and a plunger assembly extending into the bore. The plunger assembly has a rectangular key. The needle assembly has a key hole which matches the key, so that the key may be inserted into the key hole. After conventional use the plunger is rotated to lock the key within the key hole, and the plunger withdrawn to retract the needle through a resilient elastomeric seal into the syringe, rendering it inoperable and harmless.

It is apparent that numerous innovations for retractable needles have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a retractable needle syringe that avoids the disadvantages of the prior art.

ANOTHER OBJECT of the present invention is to provide a retractable needle syringe that is simple and inexpensive to manufacture.

STILL ANOTHER OBJECT of the present invention is to provide a retractable needle syringe that is simple to use.

BRIEFLY STATED, YET ANOTHER OBJECT of the present invention is to provide a retractable needle syringe that includes a barrel assembly, a plunger assembly, and a needle assembly. The plunger assembly is movably mounted in the barrel assembly. And, the needle assembly is movably mounted in the barrel assembly and engagable with the plunger assembly, so that after the retractable needle syringe has been used, the plunger assembly is engaged with the needle assembly, the plunger assembly is pulled, and the needle assembly is drawn into the barrel assembly.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows:

FIG. 1 is a diagrammatic side elevational view of the present invention;

FIG. 2 is an enlarged diagrammatic side elevational view of the barrel assembly of the present invention;

FIG. 3 is an enlarged diagrammatic end elevational view taken generally in the direction of arrow 3 in FIG. 2;

FIG. 4 is an enlarged diagrammatic end elevational view taken generally in the direction of arrow 4 in FIG. 1;

FIG. 5 is an enlarged diagrammatic perspective view of the plunger assembly of the present invention;

FIG. 6 is a cross sectional view taken on line 6—6 in FIG. 5;

FIG. 7 is an enlarged diagrammatic side elevational view of the area generally enclosed by the dotted ellipse identified by arrow 7 in FIG. 5;

FIG. 8 is an enlarged diagrammatic perspective view of the needle assembly of the present invention;

FIG. 9 is an enlarged diagrammatic end elevational view taken generally in the direction of arrow 9 in FIG. 8; and FIG. 10 is a cross sectional view taken on line 10—10 in FIG. 9.

LIST OF REFERENCE NUMERALS UTILIZED IN THE DRAWING 20 retractable needle syringe of the present invention
22 barrel assembly
24 plunger assembly
26 needle assembly
28 barrel assembly barrel
30 barrel assembly barrel distal end
32 barrel assembly barrel distal end key
34 barrel assembly barrel proximal end
36 barrel assembly barrel proximal end key way
37 barrel assembly barrel bore
38 barrel assembly finger flange
40 barrel assembly O-ring seal
42 plunger assembly stem 44 plunger assembly stem perpendicularly intersecting fins
46 plunger assembly stem distal end
48 plunger assembly stem proximal end
50 plunger assembly plunger fin notch
52 plunger assembly thumb plate
54 plunger assembly piston assembly
56 plunger assembly piston assembly proximal disk
58 plunger assembly piston assembly piston
60 plunger assembly piston assembly distal disk
62 plunger assembly piston assembly key
64 needle assembly head
65 needle assembly head interior space
66 needle assembly head distal face
67 needle assembly head proximal face
68 needle assembly head peripheral surface
70 needle assembly needle
72 needle assembly head peripheral surface key way
74 needle assembly head proximal face key hole

DETAILED DESCRIPTION OF THE PREFERRED EMBODIMENT

Referring now to the figures in which like numerals indicate like parts, and particularly to FIG. 1, the retractable needle syringe of the present invention is shown generally at 20 and includes a barrel assembly 22, a plunger assembly 24 that is movably mounted in the barrel assembly 22, and a needle assembly 26 that is movably mounted in the barrel assembly 22 and engagable with the plunger assembly 22, so that after the retractable needle syringe 20 has been used, the plunger assembly 24 is engaged with the needle assembly 26, the plunger assembly 24 is pulled, and the needle assembly 26 is drawn into the barrel assembly 22.

The plunger assembly is longitudinally and rotatably slidably movable in the barrel assembly 22 and the needle assembly 26 is longitudinally slidably movable in the barrel assembly 22.

The configuration of the barrel assembly 22 can best be seen in FIGS. 2–4, and as such will be discussed with reference thereto.

The barrel assembly 22 includes a barrel assembly barrel 28 that is hollow and cylindrically-shaped. The barrel assembly barrel 28 of the barrel assembly 22 has a barrel assembly barrel distal end 30 with a barrel assembly barrel distal end key 32 that extends radially inwardly therefrom. The barrel assembly barrel 28 of the barrel assembly 22 further has a barrel assembly barrel proximal end 34 with a barrel assembly barrel proximal end key way 36 that is U-shaped and extends radially inwardly therefrom.

The barrel assembly barrel 28 of the barrel assembly 22 contains a barrel assembly barrel bore 37 that extends L longitudinally from, and communicates with, the barrel assembly barrel distal end 30 of the barrel assembly barrel 28 of the barrel assembly 22 to, and communicates with, the barrel assembly barrel proximal end 34 of the barrel assembly barrel 28 of the barrel assembly 22.

The barrel assembly 22 further includes a barrel assembly finger flange 38 that is generally oval-shaped and extends concentrically and perpendicularly from the barrel assembly barrel proximal end 34 of the barrel assembly barrel 28 of the barrel assembly 22, and communicates with the barrel assembly barrel bore 37 in the barrel assembly barrel 28 of the barrel assembly 22, via a central opening therein.

The barrel assembly 22 further includes a barrel assembly O-ring seal 40 that is rubber and contained in the barrel assembly barrel bore 37 in the barrel assembly barrel 28 of the barrel assembly 22, and abuts against the barrel assembly barrel distal end 30 of the barrel assembly barrel 28 of the barrel assembly 22, and communicates therewith via its central opening through which a part of the needle assembly 26 is longitudinally slidably movable.

The configuration of the plunger assembly 24 can best be seen in FIGS. 5–7, and as such will be discussed with reference thereto.

The plunger assembly 24 includes a plunger assembly stem 42 that is elongated and has a "+"-shaped cross section so as to form plunger assembly stem perpendicularly intersecting fins 44, a plunger assembly stem distal end 46 that is tapered, and a plunger assembly stem proximal end 48.

The plunger assembly stem 42 of the plunger assembly 24 is contained longitudinally in the barrel assembly barrel bore 37 in the barrel assembly barrel 28 of the barrel assembly 22, with one fin of the plunger assembly stem perpendicularly intersecting fins 44 of the plunger assembly stem 42 of the plunger assembly 24 selectively engaging the barrel assembly barrel proximal end key way 36 on the barrel assembly barrel proximal end 34 of the barrel assembly barrel 28 of the barrel assembly 22 for longitudinal slidable movement therein, and with the plunger assembly stem proximal end 48 of the plunger assembly stem 42 of the plunger assembly 24 being extendable past the barrel assembly finger flange 38 of the barrel assembly 22.

The one fin of the plunger assembly stem perpendicularly intersecting fins 44 of the plunger assembly stem 42 of the plunger assembly 24 that selectively engages the barrel assembly barrel proximal end key way 36 on the barrel assembly barrel proximal end 34 of the barrel assembly barrel 28 of the barrel assembly 22 has a plunger assembly plunger fin notch 50 therein that is rectangular-shaped and disposed in close proximity to the plunger assembly plunger proximal end 48 of the plunger assembly stem 42 of the plunger assembly 24, and when it receives the barrel assembly barrel proximal end key way 36 on the barrel assembly barrel proximal end 34 of the barrel assembly barrel 28 of the barrel assembly 22, the plunger assembly stem 42 of the plunger assembly 24 is allowed to rotate.

The plunger assembly 24 further includes a plunger assembly thumb plate 52 that extends concentrically and perpendicularly from the plunger assembly stem proximal end 48 of the plunger assembly stem 42 of the plunger assembly 24, and is external of, and abutable against, the barrel assembly finger flange 38 of the barrel assembly 22.

The plunger assembly 24 further includes a plunger assembly piston assembly 54 that includes a plunger assembly piston assembly proximal disk 56 that extends concentrically and perpendicularly from the plunger assembly stem distal end 46 of the plunger assembly stem 42 of the plunger assembly 24.

The plunger assembly piston assembly 54 of the plunger assembly 24 further includes a plunger assembly piston assembly piston 58 that is rubber and slidably movable in the barrel assembly barrel bore 37 in the barrel assembly barrel 28 of the barrel assembly 22 when pressure is applied to the plunger assembly thumb plate 52 of the plunger assembly 24.

The plunger assembly piston assembly piston 58 of the plunger assembly piston assembly 54 of the plunger assembly 24 abuts against, and extends concentrically from, the plunger assembly piston assembly proximal disk 56 of the plunger assembly piston assembly 54 of the plunger assembly 24, and has a diameter sufficient to allow longitudinal slidable movement in the barrel assembly barrel bore 37 in the barrel assembly barrel 28 of the barrel assembly 22 while preventing fluid leakage between the plunger assembly piston assembly piston 58 of the plunger assembly piston assembly 54 of the plunger assembly 24 and the barrel assembly barrel bore 37 in the barrel assembly barrel 28 of the barrel assembly 22.

The plunger assembly piston assembly 54 of the plunger assembly 24 further includes a plunger assembly piston assembly distal disk 60 that abuts against, and extends concentrically from, the plunger assembly piston assembly piston 58 of the plunger assembly piston assembly 54 of the plunger assembly 24.

The plunger assembly piston assembly 54 of the plunger assembly 24 further includes a plunger assembly piston assembly key 62 that is T-shaped and extends concentrically and perpendicularly from the plunger assembly piston assembly distal disk 60 of the plunger assembly piston assembly 54 of the plunger assembly 24, and collinearly with the plunger assembly stem 42 of the plunger assembly 24.

The configuration of the needle assembly 26 can best be seen in FIGS. 8–10, and as such will be discussed with reference thereto.

The needle assembly 26 includes a needle assembly head 64 that is cylindrically-shaped and hollow so as to have a needle assembly head interior space 65 therein, and is slidably movable in the barrel assembly barrel bore 37 in the barrel assembly barrel 28 of the barrel assembly 22.

The needle assembly head 64 of the needle assembly 26 has a needle assembly head distal face 66 which is abutable against the barrel assembly O-ring seal 40 of the barrel assembly 22, a needle assembly head proximal face 67 that is opposite to the needle assembly head distal face 66 of the needle assembly head 64 of the needle assembly 26, and a needle assembly head peripheral surface 68.

The needle assembly 26 further has a needle assembly needle 70 that extends concentrically and perpendicularly from the needle assembly head distal face 66 of the needle assembly head 64 of the needle assembly 26, and is in fluid communication with the needle assembly head interior space 65 in the needle assembly head 64 of the needle assembly 26, and is slidably movable through the center opening in the barrel assembly O-ring seal 40 of the barrel assembly 22 and through the barrel assembly barrel distal end 30 of the barrel assembly barrel 28 of the barrel assembly 22.

The needle assembly head peripheral surface 68 of the needle assembly head 64 of the needle assembly 26 has a needle assembly head peripheral surface key way 72 that extends longitudinally thereacross and selectively engages the barrel assembly barrel distal end key 32 on the barrel assembly barrel distal end 30 of the barrel assembly barrel 28 of the barrel assembly 22, and when engaged therewith prevents the needle assembly 26 from rotating in the barrel assembly barrel bore 37 in the barrel assembly barrel 28 of the barrel assembly 22 so as to assure stability and rigidity of the needle assembly needle 70 of the needle assembly 26 during injection.

The needle assembly head proximal face 67 of the needle assembly head 64 of the needle assembly 26 has a needle assembly head proximal face key hole 74 that is in communication with the needle assembly head interior space 65 in the needle assembly head 64 of the needle assembly 26.

The needle assembly head proximal face key hole 74 in the needle assembly head proximal face 67 of the needle assembly head 64 of the needle assembly 26 is so shaped so as to allow the plunger assembly piston assembly key 62 of the plunger assembly piston assembly 54 of the plunger assembly 24 to pass therethrough and enter into the needle assembly head interior space 65 in the needle assembly head 64 of the needle assembly 26, but preventing the plunger assembly piston assembly key 62 of the plunger assembly piston assembly 54 of the plunger assembly 24 from passing thereout when the plunger assembly piston assembly key 62 of the plunger assembly piston assembly 54 of the plunger assembly 24 is rotated via the rotation of the plunger assembly thumb plate 52 of the plunger assembly 24.

In operation, after the retractable needle syringe 20 has been used, the plunger assembly piston assembly key 62 of the plunger assembly piston assembly 54 of the plunger assembly 24 is passed through the needle assembly head proximal face key hole 74 in the needle assembly head proximal face 67 of the needle assembly head 64 of the needle assembly 26 via the plunger assembly thumb plate 52 of the plunger assembly 24, which causes the plunger assembly plunger fin notch 50 in the one fin of the plunger assembly stem perpendicularly intersecting fins 44 of the plunger assembly stem 42 of the plunger assembly 24 to become aligned with and clear the barrel assembly barrel proximal end key way 36 on the barrel assembly barrel proximal end 34 of the barrel assembly barrel 28 of the barrel assembly 22, which allows the plunger assembly stem 42 of the plunger assembly 24 to be rotated via the rotation of the plunger assembly thumb plate 52 of the plunger assembly 24, which causes the plunger assembly piston assembly key 62 of the plunger assembly piston assembly 54 of the plunger assembly 24 to rotate and become engaged in the needle assembly head interior space 65 in the needle assembly head 64 of the needle assembly 26 with the needle assembly 26 being prevented from rotating by virtue of the needle assembly head peripheral surface key way 72 on the needle assembly head peripheral surface 68 of the needle assembly head 64 of the needle assembly 26 engaging the barrel assembly barrel distal end key 32 on the barrel assembly barrel distal end 30 of the barrel assembly barrel 28 of the barrel assembly 22, which causes the plunger assembly 24 to become engaged with the needle assembly 26, so that when the plunger assembly thumb plate 52 of the plunger assembly 24 is pulled, the plunger assembly 24 slides up the barrel assembly 22 taking the needle assembly 26 with it and causing the needle assembly needle 70 of the needle assembly 26 to become retracted into the barrel assembly 22.

It will be understood that each of the elements described above, or two or more together, may also find a useful application in other types of constructions differing from the types described above.

While the invention has been illustrated and described as embodied in a retractable needle syringe, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A retractable needle syringe, comprising:
   a) a barrel assembly;
   b) a plunger assembly movably mounted in said barrel assembly; and c) a needle assembly movably mounted in said barrel assembly and engagable with said plunger assembly, so that after said retractable needle syringe has been used, said plunger assembly is engaged with said needle assembly, said plunger assembly is pulled, and said needle assembly is drawn into said barrel assembly, wherein said barrel assembly includes a barrel that is hollow and cylindrically-shaped and has a distal end with a key thereat that extends radially inwardly therefrom, and a proximal end with a key way thereat that is U-shaped and extends radially inwardly therefrom.

2. The syringe as defined in claim 1, wherein said plunger assembly is longitudinally and rotatably slidably movable in said barrel assembly and said needle assembly is longitudinally slidably movable in said barrel assembly.

3. The syringe as defined in claim 1, wherein said barrel of said barrel assembly contains a bore that extends longitudinally from, and communicates with, said distal end of said barrel of said barrel assembly to, and communicates with, said proximal end of said barrel of said barrel assembly.

4. The syringe as defined in claim 3, wherein said barrel assembly further includes a finger flange that is generally oval-shaped and extends concentrically and perpendicularly from said proximal end of said barrel of said barrel assembly, and communicates with said bore in said barrel of said barrel assembly, via a central opening therein.

5. The syringe as defined in claim 4, wherein said barrel assembly further includes an O-ring seal that is rubber and contained in said bore in said barrel of said barrel assembly, and abuts against said distal end of said barrel of said barrel assembly, and communicates therewith via its central opening through which a part of said needle assembly is longitudinally slidably movable.

6. The syringe as defined in claim 5, wherein said plunger assembly includes a stem that is elongated and has a "+"-shaped cross section so as to form perpendicularly intersecting fins, a distal end that is tapered, and a proximal end.

7. The syringe as defined in claim 6, wherein said stem of said plunger assembly is contained longitudinally in said bore in said barrel of said barrel assembly, with one fin of said perpendicularly intersecting fins of said stem of said plunger assembly selectively engaging said key way on said proximal end of said barrel of said barrel assembly for longitudinal slidable movement therein, and with said proximal end of said stem of said plunger assembly being extendable past said finger flange of said barrel assembly.

8. The syringe as defined in claim 7, wherein said one fin of said perpendicularly intersecting fins of said stem of said plunger assembly that selectively engages said key way on said proximal end of said barrel of said barrel assembly has a notch therein that is rectangular-shaped and disposed in close proximity to said proximal end of said stem of said plunger assembly, and when it receives said key way on said proximal end of said barrel of said barrel assembly, said stem of said plunger assembly is allowed to rotate.

9. The syringe as defined in claim 8, wherein said plunger assembly further includes a thumb plate that extends concentrically and perpendicularly from said proximal end of said stem of said plunger assembly, and is external of, and abutable against, said finger flange of said barrel assembly.

10. The syringe as defined in claim 9, wherein said plunger assembly further includes a piston assembly that includes a proximal disk that extends concentrically and perpendicularly from said distal end of said stem of said plunger assembly.

11. The syringe as defined in claim 10, wherein said piston assembly of said plunger assembly further includes a piston that is rubber and slidably movable in said bore in said barrel of said barrel assembly when pressure is applied to said thumb plate of said plunger assembly.

12. The syringe as defined in claim 11, wherein said piston of said piston assembly of said plunger assembly abuts against, and extends concentrically from, said proximal disk of said piston assembly of said plunger assembly, and has a diameter sufficient to allow longitudinal slidable movement in said bore in said barrel of said barrel assembly while preventing fluid leakage between said piston of said piston assembly of said plunger assembly and said bore in said barrel of said barrel assembly.

13. The syringe as defined in claim 12, wherein said piston assembly of said plunger assembly further includes a distal disk that abuts against, and extends concentrically from, said piston of said piston assembly of said plunger assembly.

14. The syringe as defined in claim 13, wherein said piston assembly of said plunger assembly further includes a key that is T-shaped and extends concentrically and perpendicularly from said distal disk of said piston assembly of said plunger assembly, and collinearly with said stem of said plunger assembly.

15. The syringe as defined in claim 14, wherein said needle assembly includes a head that is cylindrically-shaped and hollow so as to have an interior space therein, and is slidably movable in said bore in said barrel of said barrel assembly.

16. The syringe as defined in claim 15, wherein said head of said needle assembly has a distal face which is abutable against said O-ring seal of said barrel assembly, a proximal face that is opposite to said distal face of said head of said needle assembly, and a peripheral surface.

17. The syringe as defined in claim 16, wherein said needle assembly further includes a needle that extends concentrically and perpendicularly from said distal face of said head of said needle assembly, and is in fluid communication with said interior space in said head of said needle assembly, and is slidably movable through said center opening in said O-ring seal 40 of said barrel assembly and said distal end of said barrel of said barrel assembly.

18. The syringe as defined in claim 17, wherein said peripheral surface of said head of said needle assembly has a key way that extends longitudinally thereacross and selectively engages said key on said distal end of said barrel of said barrel assembly, and when engaged therewith prevents said needle assembly from rotating in said bore in said barrel of said barrel assembly so as to assure stability and rigidity of said needle of said needle assembly during injection.

19. The syringe as defined in claim 18, wherein said proximal face of said head of said needle assembly has a key hole therein that is in communication with said interior space in said head of said needle assembly.

20. The syringe as defined in claim 19, wherein said key hole in said proximal face of said head of said needle assembly is so shaped so as to allow said key of said piston assembly of said plunger assembly to pass therethrough and enter into said interior space in said head of said needle assembly, but preventing said key of said piston assembly of said plunger assembly from passing thereout when said key of said piston assembly of said plunger assembly is rotated via rotation of said thumb plate of said plunger assembly, so that after said retractable needle syringe has been utilized, said key of said piston assembly of said plunger assembly is passed through said key hole in said proximal face of said head of said needle assembly, which causes said notch in said one fin of said perpendicularly intersecting fins of said stem of said plunger assembly to become aligned with and clear said key way on said proximal end of said barrel of said barrel assembly, which allows said stem of said plunger assembly to be rotated via said rotation of said thumb plate of said plunger assembly, which causes said key of said piston assembly of said plunger assembly to rotate and become engaged in said interior space in said head of said needle assembly with said needle assembly being prevented from rotating by virtue of said key way on said peripheral surface of said head of said needle assembly engaging said key on said distal end of said barrel of said barrel assembly, which causes said plunger assembly to become engaged with said needle assembly, so that when said thumb plate of said plunger assembly is pulled, said plunger assembly slides up said barrel assembly taking said needle assembly with it and causing said needle of said needle assembly to become retracted into said barrel assembly.

* * * * *